US007951370B2

(12) United States Patent
Balderes et al.

(10) Patent No.: US 7,951,370 B2
(45) Date of Patent: May 31, 2011

(54) ANTI-TYRP1 ANTIBODIES

(75) Inventors: Paul J. Balderes, New York, NY (US); Xiaoqiang Kang, Plainsboro, NJ (US)

(73) Assignee: ImClone LLC, New York, NY (US)

( * ) Notice: Subject to any disclaimer, the term of this patent is extended or adjusted under 35 U.S.C. 154(b) by 153 days.

(21) Appl. No.: 12/401,800

(22) Filed: Mar. 11, 2009

(65) Prior Publication Data

US 2009/0232823 A1 Sep. 17, 2009

Related U.S. Application Data

(60) Provisional application No. 61/069,199, filed on Mar. 12, 2008.

(51) Int. Cl.
*A61K 39/395* (2006.01)
*C12P 21/08* (2006.01)

(52) U.S. Cl. ............... 424/133.1; 424/138.1; 530/387.3; 530/387.7

(58) Field of Classification Search ........................ None
See application file for complete search history.

(56) References Cited

U.S. PATENT DOCUMENTS

| 4,798,790 | A | 1/1989 | Thomson et al. |
| 4,946,778 | A | 8/1990 | Ladner et al. |
| 6,168,946 | B1 | 1/2001 | Houghton et al. |

FOREIGN PATENT DOCUMENTS

| EP | 239400 | 9/1987 |
| EP | 332424 | 9/1989 |
| EP | 338745 | 10/1989 |
| EP | 1411124 | 4/2008 |
| WO | WO 88/09344 | 12/1988 |
| WO | WO 89/09622 | 10/1989 |
| WO | WO 91/14775 | 10/1991 |
| WO | WO 92/01047 | 1/1992 |
| WO | WO 93/11236 | 6/1993 |
| WO | WO 93/21319 | 10/1993 |
| WO | WO 96/40249 | 12/1996 |

OTHER PUBLICATIONS

Balders, et al., 95th Annual Meeting of AACR, Orlando, FL. (2004).
Burdon, et al., Eds., Laboratory Techniques in Biochemistry and Molecular Biology, vol. 13, Elsevier Science Publishers, Amsterdam; New York (1985).
Campbell, Monoclonal, Antibody Technology, The Production and Characterization of Rodent and Human Hybridomas, Elsevier Science Publishers, Amsterdam; New York (1984).
Clynes, et al., Proc. Natl. Acad. Sci. USA 95: 652-656 (1998).
Clynes, et al., Nat. Med. 6: 443-446 (2000).
Dakour, et al., Melanoma Res. 3: 331-336 (1993).
Hara, et al., J. Exp. Med. 182: 1609-1614 (1995).
Hawkins, et al., J. Mol. Biol. 226: 889-896 (1992).
Huse, et al., Science 246: 1275-1281 (1989).
Jimbow, et al., Pigment Cell Res. 10: 206-213 (1997).
Jones, Genetics 85: 12 (1977).
Kabat, et al., Ann. NY Acad. Sci. 190: 382-393 (1971).
Kabat, et al., U.S. Department of Health and Human Services, NIH Publication No. 91-3242 (1991).
Kaufman, et al., J. Mol. Biol. 159: 601-664 (1982).
Kingsman, et al., Gene 7: 141 (1979).
Kobayashi, et al., EMBO J. 13, No. 24 5818-5825 (1994).
Kohler, et al., Nature 256: 495-497 (1975).
Lamoyi, et al., J. Immunol. Methods 56: 235-243 (1983).
Low, et al., J. Mol. Biol. 250: 359-368 (1996).
Morrison, et al., Proc. Natl. Acad. Sci. USA 81: 6851-6855 (1984).
Nielsen, et al., Prot. Eng. 10: 1-6 (1997).
Parham, J. Immunol. 131: 2895-2902 (1983).
Patel, et al. Hum. Antibodies 16: 127-136 (2007).
Patel, et al., AACR-NCI-EORTC Int. Conf., Boston (2003).
Patel, et al., Annual Meeting of American Assoc. of Can. Res. Anaheim, CA (2005).
Pearson, et al., Proc. Natl. Acad. Sci. USA 85: 2444-2448 (1988).
Sakai, Melanoma Res. 7: 83-95 (1997).
Sambrook, et al., Molecular Cloning: A Laboratory Manual, 2nd ed., Cold Spring Harbor Laboratory Press (1989).
Scahill, et al., Proc. Natl. Acad. Sci. USA 80: 4654-4659 (1983).
Shibahara, et al., Nucleic Acids Res. 14(6): 2413-2427 (1986).
Shokri, et al., Appl. Microbiol. Biotechnol. 60(6): 654-64 (2003).
Southern, et al., J. Mol. Appl. Genet. 1: 327-341 (1982).
Stinhcomb, et al., Nature 282: 39 (1979).
Subramani, et al., Mol. Cell. Biol. 1: 854-864 (1981).
Takechi, et al., Clin. Cancer Res. 2: 1837-1842 (1996).
Urlaub, et al., Proc. Natl. Acad. Sci. USA 77: 4216-4220 (1980).
Vijayasaradhi, et al., J. Exp. Med. 171: 1375-1380 (1990).
Von Heinje, et al., Nucl. Acids Res. 14: 4683-4690 (1986).
Welt, et al., Proc. Natl. Acad. Sci. USA 84: 4200-4204 (1987).
Xu, et al., J. Invest. Dermatol. 109: 788-795 (1997).
Yang, et al., J. Mol. Biol. 254: 392-403 (1995).
Anderson, et al., Oncology 9 (11): 1149-1158 (1995).
Bevaart, et al., Cancer Res. 66 (3): 1261-1264 (2006).
O'Day, et al., Cancer Control 9 (1): 31-38 (2002).

*Primary Examiner* — Sheela J Huff
(74) *Attorney, Agent, or Firm* — Nicole Woods

(57) ABSTRACT

The present invention provides for fully human antibodies and chimeric antibodies that bind human TYRP1 antigen with an affinity comparable to or higher than TA99, a murine antibody specific to TYRP1. The invention further provides polynucleic acids and host cells that encode and express these antibodies. The invention also provides for methods of modulating activity of TYRP1, treating growth of a cancer cell, and treating a malignant melanoma in mammals by administering an effective amount of an antibody either alone or in combination with an anti-cancer agent or treatment.

8 Claims, No Drawings

US 7,951,370 B2

ANTI-TYRP1 ANTIBODIES

CROSS-REFERENCE

This application claims the benefit of U.S. Provisional Application No. 61/069,199 filed Mar. 12, 2008.

FIELD OF THE INVENTION

The present invention is directed to human and chimeric antibodies, including fragments or portions thereof, that are specific to human tyrosinase-related protein-1 (TYRP1). The antibodies are used for treating growth of cancer cells and can be used alone or in combination with an anti-neoplastic agent or treatment.

BACKGROUND OF THE INVENTION

Human tyrosinase-related protein-1 (TYRP1), also known as gp75, (WO 91/14775) (SEQ ID NO: 28) is a melanosomal membrane glycoprotein involved in melanin biosynthesis. It is found predominantly within the melanosomes of melanocytes and is also found expressed on the cell surface of melanocytes and human melanomas.

The TYRP1 antigen is highly immunogenic. Antibodies and T-cells to TYRP1 have been identified in melanoma patients. It appears that both cellular and humoral responses are effective in eliminating melanoma in vivo. Adoptive transfer of melanoma reactive T-cells also results in tumor regression. Antibody response induced by TYRP1 vaccine also could inhibit melanoma growth and metastasis in animals.

Although a variety treatment options for melanoma have been studied including, small molecule inhibitors, chemotherapeutics, immunotherapies including vaccines (for example U.S. Pat. No. 6,168,946), gene therapy/immunostimulants, and anti-angiogenics, at the present time, there are no effective therapies for patients with melanoma. Development of new treatments for this unmet medical need is highly warranted.

Animal studies have resulted in the discovery of the antibody TA99. TA99 (IgG2a), a murine monoclonal antibody (MAb) specific for human and murine TYRP1, localizes to subcutaneous human melanoma in vivo. See Welt et al., *Proc. Natl. Acad. Sci. USA* 84: 4200-4204 (1987) and U.S. Pat. No. 4,798,790. TA99 treatment inhibited tumor growth and metastasis in mice. See Takechi et al., *Clin Cancer Res.* 2:1837-42 (1996).

Mice treated with TA99 often lose hair color (depigmentation), suggesting destruction of melanocyte in the skin. The Fc receptor-mediated effector activation appears to play a critical role in the elimination of cells targeted by TA99. The anti-tumor effect of TA99 was dramatically reduced in FcR knockout mice. See Clynes et al., *Proc. Natl. Acad. Sci. USA* 95:652-656 (1998). However, the murine nature of TA99 means it would be precluded from use as a therapeutic in humans due to potential issues of immunogenicity and further its ability to activate downstream immune effector functions would be limited.

Thus there is a need to provide alternative anti-TYRP1 antibodies which are effective in the treatment of melanoma. The present invention provides alternative anti-TYRP1 antibodies that are effective in the treatment of melanoma.

Additionally, there is a need to provide alternative anti-TYRP1 antibodies which have improved binding affinity for TYRP1 compared with those antibodies known in the art. The present invention provides alternative anti-TYRP1 antibodies which have improved binding affinity for TYRP1 compared with those antibodies known in the art.

Further, there is a need to provide alternative anti-TYRP1 antibodies which have reduced immunogenicity in humans and improved ability to activate downstream immune effector functions such as antibody dependent cellular cytotoxicity (ADCC). The present invention provides chimeric and human anti-TYRP1 antibodies which have reduced immunogenicity in humans and an improved ability to activate downstream immune effector functions such as antibody dependent cellular cytotoxicity (ADCC) compared with those antibodies known in the art.

There also remains a need to provide alternative anti-TYRP1 antibodies which have improved stability via a reduction in protein misfolding and incorrect processing. Preferred antibodies of the present invention have improved stability via reduced protein misfolding and incorrect processing.

SUMMARY OF THE INVENTION

The present invention is directed to human and chimeric monoclonal antibodies, and fragments thereof, that bind to the melanoma antigen TYRP1 (SEQ ID NO:28).

One embodiment of the present invention is a monoclonal antibody that specifically binds human TYRP1 with a dissociation constant, $K_D$, at ambient laboratory temperature (20° C.-25° C.), in the range from $0.1 \times 10^{-9}$ M to $1.6 \times 10^{-9}$ M, wherein said $K_D$ values are determined by surface plasmon resonance. In other embodiments of the present invention, the monoclonal antibody is chimeric or human. Fragments of such antibodies, which fragments retain the ability to specifically bind human TYRP1, are part of the invention, even though dissociation constants for such fragments are not in the specified range.

In other embodiments of the present invention, the monoclonal antibody specifically binds human TYRP1 with a $K_D$ of about $0.1 \times 10^{-9}$ M to about $1.2 \times 10^{-9}$ M, about $0.1 \times 10^{-9}$ M to about $0.8 \times 10^{-9}$ M, about $0.1 \times 10^{-9}$ M to about $0.4 \times 10^{-9}$ M, about $0.2 \times 10^{-9}$ M to about $1.2 \times 10^{-9}$ M, about $0.2 \times 10^{-9}$ M to about $0.8 \times 10^{-9}$ M, about $0.2 \times 10^{-9}$ M to about $0.4 \times 10^{-9}$ M, about $0.2 \times 10^{-9}$ M to about $0.3 \times 10^{-9}$ M, or about $0.28 \times 10^{-9}$ M.

One embodiment of the present invention is an antibody or fragment thereof that binds TYRP1 comprising a CDRH1 having the sequence GYTFTSYAMN (SEQ ID NO:1), a CDRH2 having the sequence WINTNTGNPTYAQGFTG (SEQ ID NO:2), a CDRH3 having the sequence RYSSSW-YLDY (SEQ ID NO:3), a CDRL1 having the sequence RASQSVSSYLA (SEQ ID NO:4), a CDRL2 having the sequence DASNRAT (SEQ ID NO:5), and a CDRL3 having the sequence QQRSNWLMYT (SEQ ID NO:6), wherein said antibody further comprises an amino acid substitution within one of said CDR sequences. In another embodiment, the aforementioned CDRs do not have an amino acid substitution in one of the CDR sequences. In yet another embodiment, the antibody having the aforementioned CDRs specifically binds human TYRP1 with a dissociation constant $K_D$ in the range from $0.1 \times 10^{-9}$ M to $1.6 \times 10^{-9}$ M.

In another embodiment of the present invention, the antibody or fragment thereof that specifically binds TYRP1, comprising a CDRH1 having the sequence GFNIKDYFLH (SEQ ID NO:7), a CDRH2 having the sequence WINPD-NGNTVYDPKFQG (SEQ ID NO:8), a CDRH3 having the sequence DYTYEKAALDY (SEQ ID NO:9), a CDRL1 having the sequence RASGNIYNYLA (SEQ ID NO:10), a CDRL2 having the sequence DAKTLAD (SEQ ID NO:11), and a CDRL3 having the sequence QHFWSLPFT (SEQ ID NO:12), further comprises an amino acid substitution within one of said CDR sequences. In another embodiment, the aforementioned CDRs (SEQ ID NOs:7-12) do not have any amino acid substitutions.

Another embodiment of the present invention is an antibody or fragment thereof that binds TYRP1, and comprises a VL having the sequence:

```
                                           (SEQ ID NO: 16)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWLMYTFG

QGTKLEIK
``` and a VH sequence of

```
                                           (SEQ ID NO: 13)
QVQLVQSGSELKKPGASVKISCKASGYTFTSYAMNWVRQAPGQGLECMGW
INTNTGNPTYAQGFTGRFVFSMDTSVSTAYLQISSLKAEDTAIYYCAPRY
SSSWYLDYWGQGTLVTVSS
or
                                           (SEQ ID NO: 14)
QVQLVQSGSELKKPGASVKISCKASGYTFTSYAMNWVRQAPGQGLESMGW
INTNTGNPTYAQGFTGRFVFSMDTSVSTAYLQISSLKAEDTAIYYCAPRY
SSSWYLDYWGQGTLVTVSS.
```

Another embodiment of the present invention is a monoclonal antibody comprising a heavy chain of SEQ ID NO: 29 and a light chain of SEQ ID NO: 32; or a heavy chain of SEQ ID NO: 30 and a light chain of SEQ ID NO: 32. In one embodiment, an antibody comprises two heavy chains of SEQ ID NO: 29 and two light chains of SEQ ID NO: 32, or comprises two heavy chains of SEQ ID NO: 30 and two light chains of SEQ ID NO: 32. TYRP1-binding fragments of such antibodies are part of the invention.

The present invention is also directed to isolated DNAs encoding such antibodies and portions thereof. Other embodiments of the present invention include: an isolated polynucleic acid comprising a nucleotide sequence encoding the antibody, or a fragment thereof; an expression vector comprising said nucleotide sequence linked to an expression sequence or a recombinant host cell comprising said expression vector or a recombinant host cell or a progeny thereof, wherein said cell expresses the antibody, or fragment thereof. Yet another embodiment of the present invention is a method of producing or purifying an antibody, or fragment thereof, comprising culturing said cells under conditions permitting expression of the antibody or fragment thereof.

Additionally, the present invention is directed to methods of inhibiting growth of a cancer cell, and methods of treating melanoma, all in mammals, by administering an effective amount of antibody. One embodiment of the present invention is using the previously described antibodies or fragments thereof as a medicament. In yet another embodiment, the previously described antibodies or fragments thereof are to be used in the treatment of cancer, including but not limited to malignant melanoma.

In another embodiment, the invention provides the use of an antibody of the invention for the manufacture of a medicament for the treatment of cancer. In a preferred embodiment the cancer is malignant melanoma.

The antibodies may be used alone or in combination with an anti-neoplastic agent or treatment. One embodiment of the present invention is using the previously described antibodies in combination with an additional anti-cancer agent or treatment. In yet another embodiment, the anti-cancer agent is dacarbazine.

DETAILED DESCRIPTION OF THE INVENTION

The present invention provides for human and chimeric antibodies, and fragments thereof, specific to the TYRP1 antigen, as well as isolated or purified polynucleotide sequences encoding the antibodies. Antibodies of the present invention can be used to treat neoplastic diseases, including solid and non-solid tumors, and for treatment of hyperproliferative disorders. The term antibody includes fragments that bind TYRP-1, unless otherwise noted. Binding parameters herein are for full-length antibodies, not fragments, which will necessarily have different binding parameters because of their different size.

Naturally occurring antibodies typically have two identical heavy chains and two identical light chains with each light chain covalently linked to a heavy chain by an inter-chain disulfide bond. Multiple disulfide bonds further link the two heavy chains to one another. As used herein, the term "antibody" includes immunoglobulin molecules comprising 4 polypeptide chains, two heavy (H) chains and two light (L) chains inter-connected by disulfide bonds. Individual chains can fold into domains having similar sizes (110-125 amino acids) and structures, but different functions.

The light chain can comprise one variable domain (abbreviated herein as VL) and/or one constant domain (abbreviated herein as CL). The light chains of antibodies (immunoglobulins) are either kappa (K) light chains or lambda (λ) light chains. The expression VL, as used herein, is intended to include both the variable regions from kappa-type light chains (Vκ) and from lambda-type light chains (Vλ). The light chain constant region is comprised of one domain, CL.

The heavy chain can also comprise one variable domain (abbreviated herein as VH) and/or, depending on the class or isotype of antibody, three or four constant domains (CH1, CH2, CH3 and CH4) (abbreviated herein collectively as CH). In humans, the isotypes are IgA, IgD, IgE, IgG, and IgM, with IgA and IgG further subdivided into subclasses or subtypes ($IgA_{1-2}$ and $IgG_{1-4}$). The present invention includes antibodies of any of the aforementioned classes or subclasses (isotypes). Human $IgG_1$ is the preferred isotype for the antibodies of the present invention.

Generally, the variable domains show considerable amino acid sequence variability from one antibody to the next, particularly at the location of the antigen-binding site. Three regions, called hypervariable or complementarity-determining regions (CDRs), are found in each of VL and VH, which are supported by less variable regions called framework regions (FR). Amino acids are assigned to a particular CDR region or domain in accordance with Kabat convention (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)). Each VH and VL is composed of three CDRs and four FRs, arranged from amino-terminus to carboxy-terminus in the following order: FR1-CDR1-FR2-CDR2-FR3-CDR3-FR4.

The portion of an antibody consisting of VL and VH domains is designated Fv (Fragment variable) and constitutes the antigen-binding site. Single chain Fv (scFv) is an antibody fragment containing a VL domain and a VH domain on one polypeptide chain, wherein the N terminus of one domain and the C terminus of the other domain are joined by a flexible linker (see, e.g., U.S. Pat. No. 4,946,778 (Ladner et al.); WO 88/09344, (Huston et al.); WO 92/01047 (McCafferty et al.) describes the display of scFv fragments on the surface of soluble recombinant genetic display packages, such as bacteriophage.

The peptide linkers used to produce the single chain antibodies can be flexible peptides selected to assure that the proper three-dimensional folding of the VL and VH domains occurs. The linker is generally 10 to 50 amino acid residues. Preferably, the linker is 10 to 30 amino acid residues. More preferably the linker is 12 to 30 amino acid residues. The most preferable linker is 15 to 25 amino acid residues. An example of such linker peptides includes (Gly-Gly-Gly-Gly-Ser)$_3$.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Contaminant components of its natural environment are materials which would interfere with diagnostic or therapeutic uses for the antibody, and may include enzymes, hormones, and other proteinaceous or non-proteinaceous solutes. Examples of isolated antibodies include an antibody that has been affinity purified, an antibody that has been made by a hybridoma or other cell line in vitro, and a human antibody derived from a transgenic mouse.

The term "monoclonal antibody," as used herein, refers to an antibody obtained from a population of substantially homogeneous antibodies, e.g. the individual antibodies comprising the population are substantially identical except for possible naturally occurring mutations or minor post-translational variations that may be present. Monoclonal antibodies are highly specific, being directed against a single antigenic site (also known as determinant or epitope). Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The term "antibodies," as used herein, also includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species (e.g., mouse or rat) or belonging to another antibody class or subclass, as well as fragments of such antibodies, so long as they exhibit the desired biological activity. See, e.g. Morrison et al., Proc. Natl. Acad. Sci. USA 81:6851-6855 (1984)). Thus, the present invention includes, for example, chimeric antibodies comprising a chimeric heavy chain and/or a chimeric light chain. The chimeric heavy chain may comprise any of the heavy chain variable (VH) regions described herein or mutants or variants thereof fused to a heavy chain constant region of a non-human antibody. The chimeric light chain may comprise any of the light chain variable (VL) regions described herein or mutants or variants thereof fused to a light chain constant region of a non-human antibody.

The term "human antibody," as used herein, includes antibodies having variable and constant regions corresponding to human germline immunoglobulin sequences (as described in Kabat, et al., (1991) *Sequences of Proteins of Immunological Interest*, 5th Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs. The human antibody can have at least one position replaced with an amino acid residue, e.g. an activity enhancing amino acid residue which is not encoded by the human germline immunoglobulin sequence. However, the term "human antibody," as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences (See, Kabat, et al., supra.).

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement-mediated cytotoxicity and ADCC. For antibodies such as IgA and IgM, which are complexes of multiple IgG like proteins, complex formation requires Fc constant domains.

Thus, antibodies of the invention include, but are not limited to, naturally occurring antibodies, antibodies, human antibodies, humanized antibodies, recombinant human antibodies, monoclonal antibodies, digestion fragments, specified portions and variants thereof, including antibody mimetics or comprising portions of antibodies that mimic the structure and/or function of an antibody or specified fragment or portion thereof; each containing at least one CDR. Functional fragments include antigen binding fragments that bind to a TYRP1 antigen. For example, antibody fragments capable of binding to TYRP1 or a portion thereof, and which are embraced by the present invention include bivalent fragments such as (Fab')$_2$ with inter-chain disulfide bonds intact, monovalent fragments such as Fab (Fragment, antigen binding) which refers to the fragments of the antibody consisting of VL CL VL CH1 domains and do not retain the heavy chain hinge region (e.g., by papain digestion), fabs which retain the heavy chain hinge region, facb (e.g., by plasmin digestion), F(ab')$_2$, Fab' which lack disulfide bonds, pFc' (e.g., by pepsin or plasmin digestion), Fd (e.g., by pepsin digestion, partial reduction and re-aggregation) and Fv or scFv (e.g., by molecular biology techniques). Antibody fragments are also intended to include, e.g. domain deleted antibodies, linear antibodies, single chain antibodies, scFv, single domain antibodies, multivalent single chain antibodies, multi-specific antibodies formed from antibody fragments including diabodies, triabodies, and the like that bind specifically with antigens.

The hinge region separates the Fab and Fc portions of the antibody, providing for mobility of Fabs relative to each other and relative to Fc, as well as including multiple disulfide bonds for covalent linkage of the two heavy chains.

The antibodies, or fragments thereof, of the present invention are specific for TYRP1. Antibody specificity refers to selective recognition of the antibody for a particular epitope of an antigen. Antibodies, or fragments thereof, of the present invention, for example, can be mono-specific, bi-specific, or multi-specific. Bi-specific antibodies (BsAbs) are antibodies that have two different antigen-binding specificities or sites. Multi-specific antibodies have more than two different antigen-binding specificities or sites. Where an antibody has more than one specificity, the recognized epitopes can be associated with a single antigen or with more than one antigen. Thus, the present invention provides bi-specific antibodies, or fragments thereof, that bind to two different antigens, with at least one specificity for TYRP1.

The present invention provides isolated antibodies or fragments thereof specific for TYRP1. The TYRP1 protein is mammalian, and is preferably human. In an especially preferred embodiment, an antibody of the invention is capable of binding to both human TYRP1 and murine TYRP1 [Shibahara et al., Nucleic Acids Res. 14(6) 2413-2427 (1986)] and is hence useful in both both pre-clinical and clinical in vivo studies. The antibodies of the invention are capable of one or more of the following activities: 1) displaying high affinity binding towards TYRP1 exclusively; and 2) inhibiting tumor growth in vitro and in vivo.

Specificity of the present antibodies, or fragments thereof, for TYRP1 can be determined based on affinity and/or avidity. Affinity, represented by the equilibrium constant for the dissociation of an antigen with an antibody ($K_D$), measures the binding strength between an antigenic determinant and an antibody-binding site.

Antibodies of the present invention, or fragments thereof, also include those for which binding characteristics have been modified or improved by direct mutation, methods of affinity maturation, phage display, or chain shuffling. Affinity and specificity can be modified or improved by mutating CDRs and screening for antigen binding sites having the desired characteristics (see, e.g., Yang et al., J. Mol. Biol., (1995) 254: 392-403). CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., J. Mol. Biol., (1992) 226: 889-896). For example, phage display vectors containing heavy and light chain variable region genes can be propagated in mutator strains of *E. coli* (see, e.g., Low et al., J. Mol. Biol., (1996) 250: 359-368). These methods of mutagenesis are illustrative of the many methods known to one of skill in the art.

A convenient way for generating substitutional variants is affinity maturation using phage display. Briefly, several CDR region sites are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity, specificity, IC50, EC50, $K_D$) as herein disclosed. In order to identify candidate CDR region sites for modification, alanine scanning mutagenesis can be performed to identify CDR region residues contributing significantly to antigen binding. Alternatively, or in addition, random mutagenesis may be performed on one or more CDR sequences at one or more residue positions, either while the CDR is operably linked to the variable region or while the CDR is independent of other variable region sequence and then the altered CDR returned to a variable region using recombinant DNA technology. Once such variant antibodies are generated and expressed, the panel of variants is subjected to screening as described herein and antibodies with superior properties in one or more relevant assays may be selected for further development.

As described herein, in addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

The present invention includes TYRP1-binding polypeptides with amino acid sequences substantially the same as the amino acid sequence of the variable or hypervariable regions of the described full-length anti-TYRP1 antibodies. Substantially the same amino acid sequence is defined herein as a sequence with at least 70%, preferably at least about 80%, and more preferably at least about 90%, 95%, 96%, 97%, 98%, or 99% homology to another amino acid sequence, as determined by the FASTA search method in accordance with Pearson and Lipman (*Proc. Natl. Acad. Sci. USA* (1988) 85:2444-8).

The antibodies of the present invention, or fragments thereof, include human antibodies having one, two, three, four, five, and/or six complementarity determining regions (CDRs) selected from the group consisting of the amino acid sequences of the CDRs as set forth in Table 1.

In another embodiment, the present antibodies, or fragments thereof, can have a heavy chain variable region of 20D7 or 20D7S and/or a light chain variable region of 20D7 or 20D7S, outlined below. 20D7 and 20D7S are particularly preferred antibodies of the present invention. These antibodies have human VH and VL framework regions (FRs) as well as human CDRs.

The present invention includes nucleic acid sequences that encode an anti-TYRP1 antibody heavy chain, comprising any one of the VH regions or a portion thereof, or any one of the VH CDRs, including any variants thereof, as disclosed herein. The invention also includes nucleic acid molecules that encode an anti-TYRP1 antibody light chain comprising any one of the VL regions or a portion thereof or any one of the VL CDRs, including any variants thereof as disclosed herein.

Each domain of the antibodies of this invention can be a complete antibody with the heavy or light chain variable domain, or it can be a functional equivalent or a mutant or derivative of a naturally-occurring domain, or a synthetic domain constructed, for example, in vitro using a technique such as one described in WO 93/11236 (Griffiths et al.). For instance, it is possible to join together domains corresponding to antibody variable domains, which are missing at least one amino acid. Also included is an antibody with one or more amino acid substitution, mutation or deletion within one of the CDR sequences. The important characterizing feature is the ability of each domain to associate with a complementary domain to form an antigen-binding site. Accordingly, the terms variable heavy and light chain fragment should not be construed to exclude variants, including variants to the CDRs, that do not have a material effect on specificity.

The antibodies of the present invention may be produced by methods known in the art. These methods include the immunological method described by Kohler and Milstein, *Nature* 256: 495-497 (1975) and Campbell, Monoclonal Antibody Technology, The Production and Characterization of Rodent and Human Hybridomas, Burdon et al., Eds., Laboratory Techniques in Biochemistry and Molecular Biology, Volume 13, Elsevier Science Publishers, Amsterdam (1985); as well as by the recombinant DNA method described by Huse et al., *Science* 246: 1275-1281 (1989).

Antibody fragments can be produced by cleaving a whole antibody, or by expressing DNA that encodes the fragment. Fragments of antibodies may be prepared by methods described by Lamoyi et al., *J. Immunol. Methods* 56: 235-243 (1983) and by Parham, *J. Immunol.* 131: 2895-2902 (1983). Such fragments may contain one or both Fab fragments or the F(ab')$_2$ fragment. Such fragments may also contain single-chain fragment variable region antibodies, i.e. scFv, diabodies, or other antibody fragments. Methods of producing such functional equivalents are disclosed in PCT Application WO 93/21319, European Patent Application No. 239,400; PCT Application WO 89/09622; European Patent Application 338,745; and European Patent Application EP 332,424.

Preferred host cells for transformation of vectors and expression of the antibodies of the present invention are mammalian cells, e.g., NSO cells (non-secreting (0) mouse myeloma cells), 293 and CHO cells and other cell lines of lymphoid origin such as lymphoma, myeloma, or hybridoma cells. Other eukaryotic hosts, such as yeasts, can be alternatively used.

The transformed host cells are cultured by methods known in the art in a liquid medium containing assimilable sources of carbon (carbohydrates such as glucose or lactose), nitrogen (amino acids, peptides, proteins or their degradation products such as peptones, ammonium salts or the like), and inorganic salts (sulfates, phosphates and/or carbonates of sodium, potassium, magnesium and calcium). The medium furthermore contains, for example, growth-promoting substances, such as trace elements, for example iron, zinc, manganese and the like.

Where it is desired to express a gene construct in yeast, a suitable selection gene for use in yeast is the trp1 gene present in the yeast plasmid YRp7. Stinchcomb et al. *Nature*, 282: 39 (1979); Kingsman et al., *Gene*, 7: 141 (1979). The trp1 gene provides a selection marker for a mutant strain of yeast lacking the ability to grow in tryptophan, for example, ATCC No. 44076 or PEP4-1. Jones, Genetics, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

The antibodies of the invention may be isolated or purified by any method known in the art, including precipitation by ammonium sulfate or sodium sulfate followed by dialysis against saline, ion exchange chromatography, affinity or immuno-affinity chromatography as well as gel filtration or zone electrophoresis. A preferred method of purification for the antibodies of the current invention is Protein-A affinity chromatography.

DNA encoding human antibodies can be prepared by recombining DNA encoding human constant regions and variable regions, other than the CDRs, derived substantially or exclusively from the corresponding human antibody regions and DNA encoding CDRs derived from a human.

Suitable sources of DNAs that encode fragments of antibodies include any cell, such as hybridomas and spleen cells, which express the full-length antibody. The fragments may be used by themselves as antibody equivalents, or may be recombined into equivalents, as described above. The DNA deletions and recombinations described in this section may be carried out by well-known methods. Another source of DNA is a phage display library of antibodies, as is known in the art. The exemplified antibodies of the current invention were made via hybridoma technology from immunized mice.

Additionally, the present invention provides expression vectors containing the polynucleotide sequences previously described operably linked to an expression sequence, a promoter and an enhancer sequence. A variety of expression vectors for the efficient synthesis of antibody polypeptide in prokaryotic systems, such as bacteria, and eukaryotic systems, including but not limited to yeast and mammalian cell culture systems, have been developed. The vectors of the present invention can comprise segments of chromosomal, non-chromosomal and synthetic DNA sequences.

Any suitable expression vector can be used. For example, prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages. An example of a vector useful in yeast is the 2μ plasmid. Suitable vectors for expression in mammalian cells include well-known derivatives of SV-40, adenovirus, retrovirus-derived DNA sequences and shuttle vectors derived from combination of functional mammalian vectors, such as those described above, and functional plasmids and phage DNA.

Additional eukaryotic expression vectors are known in the art (e.g., P. J. Southern and P. Berg, *J. Mol. Appl. Genet.* 1: 327-341 (1982); Subramani et al., *Mol. Cell. Biol.* 1: 854-864 (1981); Kaufmann and Sharp, *J. Mol. Biol.* 159: 601-664 (1982); Scahill et al., *Proc. Natl. Acad. Sci. USA* 80: 4654-4659 (1983); and Urlaub and Chasin, *Proc. Natl. Acad. Sci. USA* 77: 4216-4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The present invention also provides recombinant host cells containing the expression vectors previously described. Antibodies of the present invention can be expressed in cell lines other than in hybridomas. Nucleic acids, which comprise a sequence encoding a polypeptide according to the invention, can be used for transformation of a suitable mammalian host cell.

Cell lines of particular preference are selected based on high level of expression, constitutive expression of protein of interest and minimal contamination from host proteins. Mammalian cell lines available as hosts for expression are well known in the art and include many immortalized cell lines, such as but not limited to, NSO cells (non-secreting (0) mouse myeloma cells), mouse myeloma cells, Chinese Hamster Ovary (CHO) cells, Baby Hamster Kidney (BHK) cells and many others. Suitable additional eukaryotic cells include yeast and other fungi. Useful prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*.

These present recombinant host cells can be used to produce an antibody, or fragment thereof, by culturing the cells under conditions permitting expression of the antibody or fragment thereof and purifying the antibody or fragment thereof from the host cell or medium surrounding the host cell. Targeting of the expressed antibody or fragment for secretion in the recombinant host cells can be facilitated by inserting a signal or secretory leader peptide-encoding sequence (see, Shokri et al., (2003) Appl Microbiol Biotechnol. 60(6):654-64, Nielsen et al., Prot. Eng. (1997) 10:1-6 and von Heinje et al., (1986) Nucl. Acids Res. 14:4683-4690) at the 5' end of the antibody-encoding gene of interest. These secretory leader peptide elements can be derived from either prokaryotic or eukaryotic sequences. Accordingly suitably, secretory leader peptides are used, being amino acids joined to the N-terminal end of a polypeptide to direct movement of the polypeptide out of the host cell cytosol and secretion into the medium.

The antibodies of this invention can be fused to additional amino acid residues. Such amino acid residues can be a peptide tag, perhaps to facilitate isolation. Other amino acid residues for homing of the antibodies to specific organs or tissues are also contemplated.

Another embodiment for the preparation of antibodies in the present invention is the expression of the nucleic acid encoding the antibody according to the invention in a transgenic animal that has a substantial portion of the human antibody producing genome inserted and is rendered deficient in the production of endogenous antibodies. Transgenic animals include, but are not limited to mice, goat, and rabbit. One further embodiment of the invention includes expression of the antibody-coding gene in, for example, the mammary gland of the animal for secretion of the polypeptide during lactation.

A method of treating tumor growth in a mammal by administering to the mammal an effective amount of an antibody is also provided by the present invention. Suitable tumors to be treated according to the present invention preferably express TYRP1. While not intended to be bound by any particular mechanism, the present methods provide for treatment of the growth of cancer cells including malignant melanoma. "Treatment" or "treat", in the context of the present invention refers to therapeutic treatment including inhibiting, slowing, lessening or reversing the progress of the underlying condition or undesired physiological change associated with a disease or disorder, ameliorating clinical symptoms of a condition or preventing the appearance of clinical symptoms of the condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. "Treatment" can also mean prolonging survival as compared to expected survival if not receiving treatment. Those in need of treatment include those already with the disease. In one embodiment, the present invention can be used as a medicament.

The term "melanoma" includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, modular melanoma, lentigo malignant melanoma, acral lentiginous melanoma, invasive melanoma and familial atypical mole and melanoma (FAM-M) syndrome. In one embodiment of the invention, melanoma is a specific form of cancer. In another embodiment the melanoma can be malignant. One embodiment of the present invention would be to utilize, as described below, the presently described anti-TYRP1 antibodies to treat first line melanoma. In another embodiment, the presently described anti-TYRP1 antibodies would be first line treatment for metastatic melanoma, that is, they would be used in a first round of treatment of newly diagnosed metastatic melanoma.

In the methods of the present invention, a therapeutically effective amount of an antibody of the invention is administered to a mammal in need thereof Effective doses of the compositions of the present invention, for treatment of disorders as described herein vary depending upon many different factors, including means of administration, target site, physiological state of the patient, whether the patient is human or an animal, other medications administered, and whether treatment is prophylactic or therapeutic. The term administering as used herein means delivering the antibodies of the present invention to a mammal by any method that can achieve the result sought. They can be administered, for example, intravenously or intramuscularly. Although human antibodies of the invention are particularly useful for administration to humans, they can be administered to other mammals as well. The term mammal as used herein is intended to include, but is not limited to, humans, laboratory animals, domestic pets and farm animals. Therapeutically effective amount means an amount of antibody of the present invention that, when administered to a mammal, is effective in producing the desired therapeutic effect, such as inhibiting tumor growth. Treatment dosages may be titrated using routine methods known to those of skill in the art to optimize safety and efficacy.

The pharmaceutical compositions of the invention may include a "therapeutically effective amount" of an anti-TYRP1 antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. Dosage regimens may be adjusted to provide the optimum desired response (e.g., a therapeutic or prophylactic response).

The identification of such disease is well within the ability and knowledge of one skilled in the art. For example, human individuals who are suffering from malignant melanoma or who are at risk of developing clinically significant symptoms are suitable for administration of the present anti-TYRP1 antibodies.

The present anti-TYRP1 antibodies are administered for therapeutic treatments to a patient suffering from malignant melanoma in an amount sufficient to inhibit, or reduce the progression of the tumor or pathologic condition. Progression includes, e.g., the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. An exemplary, non-limiting range for a therapeutically effective amount of an antibody of the invention is 0.1-50 mg/kg, more preferably 3-35 mg/kg, and more preferably 5-20 mg/kg. Dosing amounts and frequencies will be determined by the physicians treating the patient and may include doses from less than 1 mg/kg to over 100 mg/kg given daily, three times per week, weekly, once every two weeks, or less often. Dose per administration may be in the range of 1-100, 2-75, or 5-60 mg/kg. It should be noted, however, that the present invention is not limited to any particular dose.

In an embodiment of the invention, anti-TYRP1 antibodies can be administered in combination with one or more other anti-neoplastic agents. Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine (DTIC). In vivo studies indicate that administering 20D7 in combination with dacarbazine (DTIC) demonstrate stronger anti-tumor activity compared to mono-therapy on a human 624mel xenograft. In one embodiment of the present invention, the presently described anti-TYRP1 antibodies are given in combination with dacarbazine. Examples of anti-metabolites include, but are not limited to, doxorubicin, daunorubicin, paclitaxel, irinotecan (CPT-11), and topotecan. When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of the tumor being treated and the route of administration of the agent. It should be emphasized, however, that the present invention is not limited to any particular dose.

In the present invention, any suitable method or route can be used to administer anti-TYRP1 antibodies of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. Parenteral routes are preferred. It should be emphasized, however, that the present invention is not limited to any particular method or route of administration.

In another aspect of the invention, an anti-TYRP1 antibody of the invention can be chemically or biosynthetically linked to one or more anti-neoplastic or anti-angiogenic agents.

The invention further contemplates anti-TYRP1 antibodies linked to target or reporter moieties, including by way of example only anti-neoplastic agents, other antibodies or reporters, such as radiolabled isotopes, in a diagnostic system where a detectable signal-producing agent is conjugated to the antibody.

It is understood that the anti-TYRP1 antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

Moreover, included within the scope of the present invention is use of the present antibodies in vivo and in vitro for investigative or diagnostic methods, which are well known in the art. The diagnostic methods include kits, which contain antibodies of the present invention.

In one embodiment, the invention is a human monoclonal antibody, or fragment thereof, specific for TYRP1. In another embodiment, the invention is a chimeric monoclonal antibody, or fragment thereof, specific for TYRP1. In another embodiment the CDR regions of the antibody are identical to the CDR regions of CTA99. In a different embodiment the CDR regions of the antibody are identical to the CDR regions of 20D7 or 20D7S.

In one embodiment, the antibody binds to TYRP1 with a dissociation rate constant ($K_d$ or $k_{off}$) between $1.7 \times 10^{-4}$ 1/s ($sec^{-1}$, 1/seconds) and $5 \times 10^{-4}$ 1/s, as measured by surface plasmon resonance, described herein, at ambient laboratory temperature (20° C.-25° C). In another embodiment, the antibody binds to TYRP1 with a $K_d$ or $k_{off}$ between $1.7 \times 10^{-4}$ 1/s and $3.5 \times 10^{-4}$ 1/s. In a further embodiment, the antibody binds to TYRP1 with a dissociation rate constant, as measured by surface plasmon resonance, that is within 10% of the dissociation rate constant determined for 20D7, 20D7S, or CTA99 under the same conditions.

One embodiment of the present invention comprises a monoclonal antibody, or fragment thereof, specific for TYRP1 comprising one or more complementarity determining regions (CDRs) selected from the group consisting of the CDRs in Tables 1 and 2. In another embodiment, the invention is a monoclonal antibody, or fragment thereof, specific for TYRP1 having a light chain CDR1 region with the sequence: RASQSVSSYLA (SEQ ID NO:4). In another embodiment, the invention is a monoclonal antibody, or fragment thereof, specific for TYRP1 having a heavy chain CDR3 with the sequence: RYSSSWYLDY (SEQ ID NO:3). In a different embodiment, the invention is a monoclonal antibody, or fragment thereof, comprising (i) a light chain variable region selected from the group consisting of 20D7, 20D7S and CTA99 and (ii) a heavy chain variable region selected from the group consisting of 20D7, 20D7S and CTA99. In another embodiment, the invention is a monoclonal antibody, or fragment thereof, specific for TYRP1 comprising (i) a light chain variable region of CTA99 (ii) a heavy chain variable region of CTA99, and (iii) human immunoglobulin $G_1$ ($hIgG_1$) constant regions.

Another embodiment of this invention is a method of treating cancer in a mammal comprising administering to the mammal an effective amount of an antibody, or fragment thereof, of any of the embodiments already described. The invention also provides a method to treat a malignant melanoma. Another treatment method provided by this invention combines using the antibodies or fragments thereof of this invention along with administering an additional anti-cancer agent or treatment. In one treatment method, the anti-cancer agent is dacarbazine (DTIC).

It is to be understood and expected that variations in the principles of invention herein disclosed can be made by one skilled in the art and it is intended that such modifications are to be included within the scope of the present invention.

All references mentioned herein are incorporated in their entirety.

EXAMPLES

The examples that follow further illustrate the invention, but should not be construed to limit the scope in any way. They should in no way be construed, however, as limiting the broad scope of the invention. Detailed description of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et al., (1989) Molecular Cloning: A Laboratory Manual, 2nd ed., Cold Spring Harbor Laboratory Press.

Animals and Cell Lines

Maintain SKmel28, SKmel23, 624mel, 1102mel and A375 in RPMI 1640 (Invitrogen Life Technologies) with 10% heat-inactivated fetal bovine serum (HyClone Laboratories, Logan, Utah) and routinely test for Mycoplasma contamination. SKmel23 and SKmel28 were provided by Dr. Alan Houghton (Memorial Sloan-Kettering Cancer Center, New York, N.Y.). 624mel and 1102mel were obtained from Dr. Steve Rosenberg (National Cancer Institute, Bethesda, Md.). A375 was purchased from American Type Culture Collection (Manassas, Va.). Six to eight week old female Nu/Nu mice were purchased from Taconic Farms (Germantown, N.Y.).

Expression and Purification of Human and Chimeric Anti-TYRP1 Antibodies

For each antibody, engineer a suitable heavy chain nucleotide sequence, for example SEQ ID NOs 21, 22, or 23 (for 20D7, 20D7S and CTA99 respectively) into a suitable expression plasmid, for example pGSHC, and engineer a suitable light chain nucleotide sequence, for example SEQ ID No. 26 or 27 (for 20D7/20D7S and CTA99 respectively) into a suitable expression plasmid, such as pGSLC, by a suitable method such as PCR cloning. To establish a stable cell line, co-transfect in a suitable host cell line, such as NS0 cells, with linearized heavy and light chain plasmids by electroporation and culture in suitable media such as glutamine free Dulbecco's Modified Eagle Medium with dialyzed fetal calf serum and glutamine synthetase supplement. Screen clones for antibody expression by an enzyme-linked immunosorbent assay (ELISA) and select the highest producer for culture in spinner flasks. Purify antibodies by a suitable method such as protein-A affinity chromatography.

One embodiment of the present invention is the recombinant human monoclonal antibody 20D7, a full length IgG1κ targeting cell surface expressed tyrosinase-related protein-1 (TYRP1 or TRP1). The antibody is comprised of a human gamma-1 heavy chain (HC) (subgroup I) and a human kappa light chain (subgroup III). 20D7 was shown to selectively bind to human TYRP1 with high affinity and mediated potent anti-tumor activity in xenograft models by a mechanism involving activation of immune effector function.

One embodiment of the present invention is the recombinant human monoclonal antibody 20D7S, a full length IgG1κ targeting cell surface expressed tyrosinase-related protein-1 (TYRP1 or TRP1). The antibody is comprised of a human gamma-1 heavy chain (HC) (subgroup I) and a human kappa light chain (subgroup III). 20D7S was created in an effort to generate an even more stable molecule; a free cysteine residue within the heavy chain variable region (C47) was converted to a serine residue by site-directed mutagenesis. This unpaired or free cysteine has the potential to mis-pair with other cysteines that participate in intra- and inter-chain disulfide bridging of heavy and light chain polypeptides. Mis-pairing could potentially result in improper folding and processing, increasing the heterogeneity of the product and potentially its stability. The SDS PAGE gel analysis described herein confirms the presence of free light chain and free heavy chain in the preparation of 20D7, but the presence of free light chains and free heavy chains are reduced or eliminated in the preparation of 20D7S.

Another embodiment of the present invention is CTA99, a chimeric antibody with a human constant region IgG1. Murine antibody TA99 (U.S. Pat. No. 4,798,790) contains two light chains; one TA99 light chain is specific to TYRP1 and the other is from parental mouse myeloma cells. There is decreased activity because the contaminated light chain is unable to bind to TYRP1. CTA99 was constructed to remediate this flaw and thereby improve activity. In one embodiment of the present invention, CTA99 was designed with two identical heavy chains and two identical light chains. Studies described herein illustrate CTA99's increased activity and binding affinity, as well as effector functions more suitable for humans.

Tables 1 and 2 provide the amino acid sequences and SEQ ID NOs of the various CDRs of the present invention. Table 3 provides the SEQ ID NOs of the various sequences related to the present invention. Polynucleic acid sequences that encode the amino acid sequences disclosed below are also included within the scope of the present invention.

TABLE 1

Amino Acid Sequence of 20D7 and 20D7S Antibody Heavy and Light Chain Variable Region CDRs.

| | Heavy Chain | SEQ ID NO. | Light Chain | SEQ ID NO. |
|---|---|---|---|---|
| CDR1 | GYTFTSYAMN | 1 | RASQSVSSYLA | 4 |
| CDR2 | WINTNTGNPTYAQGFTG | 2 | DASNRAT | 5 |
| CDR3 | RYSSSWYLDY | 3 | QQRSNWLMYT | 6 |

TABLE 2

Amino Acid Sequence of CTA99 Antibody Heavy and Light Chain Variable Region CDRs.

| | Heavy Chain | SEQ ID NO. | Light Chain | SEQ ID NO. |
|---|---|---|---|---|
| CDR1 | GFNIKDYFLH | 7 | RASGNIYNYLA | 10 |
| CDR2 | WINPDNGNTVYDPKFQG | 8 | DAKTLAD | 11 |
| CDR3 | DYTYEKAALDY | 9 | QHFWSLPFT | 12 |

TABLE 3

Amino Acid Sequence SEQ. ID. NOs of 20D7, 20D7S, and CTA99 Antibodies

| Antibody | Heavy Chain | | | Light Chain | | |
|---|---|---|---|---|---|---|
| | With signal | Variable region | Without signal | With signal | Variable region | Without signal |
| 20D7 | 18 | 13 | 29 | 24 | 16 | 32 |
| 20D7S | 19 | 14 | 30 | 24 | 16 | 32 |
| CTA99 | 20 | 15 | 31 | 25 | 17 | 33 |

Antibodies used in experiments comprised full-length heavy and light chains without signals, as given in Table 3.

TABLE 4

Summary of Data from 20D7, 20D7S, and CTA99 Antibodies

| Antibody | Competition ELISA ($EC_{50}$) (M) | FACS (mel) | Affinity $K_D$ (M) | Human FcR binding (M) | Human ADCC (%) | Human CDC (%) |
|---|---|---|---|---|---|---|
| TA99 | $4.0 \times 10^{-10}$ | +++ | $1.7 \times 10^{-9}$ | ND | ND | ND |
| CTA99 | $1.1 \times 10^{-10}$ | +++ | $1.1 \times 10^{-9}$ | ND | 48 | 94 |
| 20D7 | $1.1 \times 10^{-10}$ | +++ | $0.28 \times 10^{-9}$ | $1.1 \times 10^{-10}$ | 42 | 100 |
| 20D7S | $0.98 \times 10^{-10}$ | +++ | $0.28 \times 10^{-9}$ | $0.97 \times 10^{-10}$ | 56 | ND |

ND = not determined.

Competition Enzyme-Linked Immunosorbent Assay (ELISA)

Coat falcon flexible 96-well flat-bottomed plates with recombinant human TYRP (0.5 ug/mL×50 μL) at 4° Celsius overnight. The next day, block the plate with 5% FBS in PBS containing 0.1% Tween-20 for 2 h at room temperature. Add various amounts of antibodies in 100 μL samples. Wash the plate 3× with PBS/Tween and add 100 μL of horseradish peroxidase-conjugated goat anti-human antibody (Biosource, Camarillo, Calif.) diluted at 1:5000 in 100 μL to the plate and incubate for one hour at room temperature (20-25° C.). Wash the plate 3× and add 50 μL /well of 3,3',5,5'-tetramethylbenzidine (TMB; KPL, Gaithersburg, Md.) substrate to the plate. Read the plates at 450 nm using a microplate reader (such as Molecular Devices).

TABLE 5

Enzyme-Linked Immunosorbent Assay (ELISA)

| Antibody | Binding to TYRP1 ($EC_{50}$) (M) |
|---|---|
| TA99 | $4.0 \times 10^{-10}$ |
| CTA99 | $1.1 \times 10^{-10}$ |
| 20D7 | $1.1 \times 10^{-10}$ |
| 20D7S | $0.98 \times 10^{-10}$ |

The half minimal effect concentration ($EC_{50}$) is measured in Molar (M). Antibodies, including human 20D7, human 20D7S and CTA99, exhibit specific binding to human TYRP1 in an ELISA assay.

Flow Cytometry

Treat 624mel cells for 1 hour on ice with either 5 μg/mL human IgG, or anti-TYRP1 MAbs in 1% BSA/PBS. Wash cells 3× in 1% BSA/PBS and incubate for 1 hour with fluorescein isothiocyanate (FITC)-labeled goat anti-human IgG. Wash cells and analyze by a suitable flow cytometer, such as Epics XL Flow Cytometer (Coulter). Flow cytometry analysis shows that 20D7S antibodies as exemplified herein exhibit binding to native TYRP1 expressing in human cell lines SKmel28 and SKmel23 as compared to control human $IgG_1$. Similarly, flow cytometry analysis shows that for CTA99 and 20D7 antibodies exemplified herein exhibit binding to native TYRP1 expressing human cell line 624mel as compared to control human $IgG_1$.

Surface Plasmon Resonance/Biacore Analysis

Measure the binding kinetics of the antibodies to recombinant human TYRP1 at ambient laboratory temperature (20° C.-25° C.) using the surface plasmon resonance, for example a Biacore biosensor (Pharmacia). Immobilize TYRP1 protein onto a CM5 research grade sensor chip and inject the antibodies at concentrations ranging from 0.5 nM to 100 nM. Acquire sensorgrams for each concentration and evaluate using the BIA Evaluations 3.2 program to determine the rate constants $k_{on}$ and $k_{off}$. $K_d$, also referred to as $k_{off}$, is the rate constant of the dissociation reaction. $K_a$, also referred to as $k_{on}$, is the rate constant of the association reaction. $K_D$ is a measure of binding affinity; calculate $K_D$ from the ratio of the rate constants $k_{off}/k_{on}$ measured in Molar (M). $K_a$, the $K_d$, and $K_D$ for the antibodies exemplified herein, TA99, CTA99, 20D7, and 20D7S, are summarized below in Table 6.

TABLE 6

Binding Kinetics of Antibodies to Recombinant Human TYRP1

| Antibody | $K_a$ (1/Ms) $k_{on}$ | $K_d$ (1/s) $k_{off}$ | $K_D$ (M) |
|---|---|---|---|
| TA99 | $9.5 \times 10^4$ | $1.6 \times 10^{-4}$ | $1.7 \times 10^{-9}$ |
| CTA99 | $2.8 \times 10^4$ | $3.0 \times 10^{-4}$ | $1.1 \times 10^{-9}$ |
| 20D7 | $6.8 \times 10^5$ | $1.9 \times 10^{-4}$ | $0.28 \times 10^{-9}$ |
| 20D7S | $6.4 \times 10^5$ | $1.8 \times 10^{-4}$ | $0.28 \times 10^{-9}$ |

Biacore analysis of the binding of 20D7 and 20D7S to human TYRP1 demonstrate substantial specific binding affinities; accordingly 20D7 and 20D7S are valid candidates for therapeutic antibodies.

Complement Dependent Cytotoxicity (CDC) Assay

Wash human melanoma cell line 624mel 3 times and bring to a concentration of $10^6$ viable cells/mL in a suitable media, such as AIM V Media (Invitrogen Life Technologies). Plate one hundred microliters of cells in 96-well, round-bottom Falcon plates and incubate with MAb 20D7 or hIgG (Jackson Immunoresearch, West Grove, Pa.) starting at 3.7 μg/mL diluted down 1:3, for 1 hr at 37° C. Add low-Tox-M Rabbit complement (Cedarlane Labs, Westbury, N.Y.) diluted 1:5 in AIM V at 50 μl/well and incubate for 1 hr at 37° C. Count cells for viability with Trypan Blue (Invitrogen Life Technologies).

Table 7 shows the percentage of cytotoxicity at various antibody concentrations in the CDC assay. The data demonstrate that 20D7 and CTA99 antibodies induce CDC against TYRP1 (+) human 624mel cells in vitro. 20D7 triggered dose-dependent complement-mediated cell lysis of 624mel cells, reaching complete cell lysis in this assay with an antibody concentration of 3.7 μg/mL. Accordingly, there is a strong immune effector response for CDC in 20D7 and CTA99. % Specific Lysis=Test % Cytotoxicity−Negative Control % Cytotoxicity.

TABLE 7

CDC Data Demonstrating Complement Activation by 20D7 and CTA99

| Antibody Concentration (μg/mL) | CTA99 | 20D7 |
| --- | --- | --- |
| 3.7 | 95% | 100% |
| 1.23 | 54% | 84% |
| 0.41 | 53% | 38% |
| 0.14 | 17% | 35% |
| 0.05 | 9.5% | 24% |

Antibody Dependent Cellular Cytotoxicity (ADCC) Against Human Melanoma In Vitro

Collect and wash 624mel cells with a suitable media, such as AIM V media (Invitrogen Life Technologies) and plate the cells at a density of 10,000 cells /well in a 100 μL volume, in a 96-well Falcon U bottom plate. Add antibodies at 5 μg/mL in a 50 μL volume and incubate at 37° C. for 0.5 hr with target cells. Effector cells were added in a volume of 50 μL at various E:T (effector:target) ratios. Plates were further incubated for 4 hrs at 37° C. After incubation, plates were spun down at 800 g, and 100 μL of supernatants were gently transferred to 96 well flat bottom plates. Lactate dehydrogenase assay reagent was added as specified by the manufacturer (Roche) and plates were read at 490 nm. Controls in assay: Target Spontaneous and Target Maximum (by adding 50 μL of 4% triton).

Lysis is dependent on the effector to target concentration with lysis of 50% of target cells occurring at an E:T ratio of 100:1. At a fixed concentration (5 μg/mL) 20D7 and CTA99 activate the lysing of 624mel cells. Table 8 shows the percentage of cell cytotoxicity in the presence of various effector cell to tumor cell ratios (E:T Ratio) in the ADCC assay. 20D7S, 20D7 and CTA99 antibodies induce ADCC against TYRP1 (+) human 624mel cells in vitro. There is a strong immune effector response for ADCC in 20D7S, 20D7 and CTA99.

% Cytotoxicity=(Experimental−target spontaneous)/ (Target Maximum−target spontaneous)×100

TABLE 8

ADCC against Human Melanoma In Vitro

| | % Cytotoxicity | | |
| --- | --- | --- | --- |
| E:T Ratio | 20D7 | 20D7S | CTA99 |
| 100:1 | 43% | 56% | 49% |
| 50:1 | 33% | 47% | 39% |
| 25:1 | 31% | 43% | 17% |
| 12.5:1 | 17% | 23% | 12% |

20D7S and 20D7 Stability Assays

Load 20D7 and 20D7S into SDS-PAGE gel (sodium dodecyl sulfate polyacrylamide gel electrophoresis). Run gels using BioRad apparatus until the bromophenol blue dye is just off. Visualize the separated proteins using Coomassie Dye.

In the SDS PAGE analysis, more stable molecules are seen as a single band with few if any free light and or heavy chains; the presence of free light chains and free heavy chains are evidence of less stable molecules. The SDS PAGE gel of 20D7 showed the presence of obvious free light and heavy chains. The SDS PAGE gel of 20D7S showed very few free light and heavy chains. Accordingly, 20D7S is a more stable IgG1 molecule than 20D7.

CTA99 and 20D7 Effectively Treat Human Melanoma Xenografts

For the following subcutaneous studies, tumor volumes are calculated by the formula $[\pi/6(W1 \times W2 \times W2)]$, where W1 represents the largest tumor diameter and W2 represents the smallest tumor diameter. % T/C=100×(Treatment Volume/Initial Volume)/(Control Volume/Initial Volume). Statistical analysis is done using traditional p-value techniques. For the subcutaneous studies the p value is calculated based on the tumor volume of animals receiving the anti-TYPR antibody verses the tumor volume of the control animals. For the following metastatic studies, tumor inhibition is measured by counting lung surface nodules. % inhibition=100×(control nodules#−treatment nodules#)/(control nodules#). Statistical analysis is done using traditional p-value techniques. For the metastatic studies the p-value is calculated based on the nodules observed in the animals receiving the anti-TYPR antibody verses the nodules observed in the control animals.

In Vivo Single Agent Activity of Anti-TYRP1 Antibody on Xenograft Models of Human Melanoma Harvest, wash and resuspend 624mel cultured cells in a 50/50 solution of Matrigel and RPMI 1640 media (10% FBS heat inactivated). For the subcutaneous tumor model, inject $2 \times 10^6$ cells subcutaneously into the left flank of nude mice. When tumors reach 200 mm$^3$, treat mice with anti-TYRP1 antibodies or control human IgG; administer antibodies 1 mg/mouse three times per week. Measure tumors with calipers twice a week and calculate % T/C. For the in vivo single agent activity of anti-TYRP1 antibody on xenograft models of human melanoma, growth of SKmel28 xenografts was inhibited by 20D7 treatment compared to human IgG control (T/C=51%; P=0.01 at day 43). Established 624mel tumors were also shown to be inhibited significantly by 20D7 treatment. Tumor growth was inhibited and reached statistical significance at day 16 post initiation of antibody treatment (T/C=44%; P=0.01). Additional human melanoma xenografts were evaluated for anti-tumor activity of 20D7. Cell lines A375 and 1102mel were shown to be significantly inhibited by single agent 20D7 11 days post antibody treatment (T/C=42%; P=0.01 and T/C=43%; P=0.004 for A375 and 1102mel respectively). Lysates of skins from different species are incubated with TA99 (5 μg/ml) for 2 hours at room temperature. The lysates are then precipitated with protein A and subjected to SDS-PAGE under reducing and non-reducing conditions using four 12% gradient gels. After electrophoresis, the gels are transferred to PVDF membrane (Invitrogen Life Technologies). The membrane is probed with 20D7S (5 μg/ml) followed by an HRP labeled anti-human IgG (Zymed, South San Francisco, Calif.). The blot is developed using a chemiluminescent substrate (KPL, Gaithersburg, Md.). The data show that 20D7 readily cross-reacts with mouse TYRP1. However, no overt toxicity was apparent in any animals treated with 20D7. Body weight and overall appearance were not significantly different in 20D7 treated animals relative to human IgG control treated mice.

In Vivo Single Agent Dose Response Activity of Anti-TYRP1 Antibody on Xenograft Models of Human Melanoma Mix Skmel28 cells in a 50/50 solution of Matrigel and RPMI 1640 media (10% FBS heat inactivated). Inject $2 \times 10^6$ cells subcutaneously into the left flank of nude mice. When tumors reach 200 mm$^3$, treat mice with anti-TYRP1 antibodies (6 mg/kg, 20 mg/kg, or 60 mg/kg) or control human IgG three times per week. Measure tumors with calipers twice a week and calculate % T/C. The dose-response study of 20D7 on SKmel28 xenografts indicated a dose-dependent anti-tumor response. Even at 6 mg/kg dose, tumors were significantly inhibited by 20D7 (T/C=69%; P<0.0001). The anti-tumor effects at each dose were statistically significant: 6 mg/kg and 20 mg/kg (T/C=50%; P=0.04), 6 mg/kg and 60 mg/kg (T/C=19%; P<0.003).

In Vivo Single Agent Activity of Anti-TYRP1 Antibody in Two Metastatic Melanoma Models B16BL6 is an aggressive and spontaneously arising murine melanoma. It forms lung metastases in nude mice after intravenous administration. Harvest, wash and resuspend cultured SKmel23 and B16BL6 cells melanoma cells in RPMI 1640 media (10% FBS heat inactivated).

Model 1: Inject $1 \times 10^5$ B16BL6 cells intravenously. On the second day after the tumor injection, administer to mice anti-TYRP1 antibodies or control human IgG, according to three different dose concentrations (200 µg/mouse, 500 µg/mouse, and 1 mg/mouse). Sacrifice mice on day 20, remove lungs, count lung surface nodules and calculate percent inhibition. Heavy metastases are detected over the surface of the lungs in human IgG treated mice; significantly fewer metastases are noted in 20D7 treated animals. All three concentrations of 20D7 reduce the level of lung metastases (Inhibition=65%, 74%, and 95%, respectively).

Model 2: Inject $1 \times 10^5$ human SKmel23 cells intravenously. On the second day after the tumor injection, administer to mice anti-TYRP1 antibodies or control human IgG, according to two different dose concentrations (200 µg/mouse and 500 µg/mouse). Sacrifice mice on day 20, remove lungs, count lung surface nodules and calculate percent inhibition. Metastatic nodules are significantly reduced by treatment with 20D7 or CTA99 at 200 µg/dose and at 500 µg/dose. 20D7 reduced metastasis by 58% and 73% respectively. CTA99 reduced metastasis by 63% and 75% respectively. These results demonstrate that in two separate models, melanoma metastasis is inhibited by 20D7 and CTA99.

In Vivo Comparative Studies of 20D7 and 20D7S Inhibition of Tumor Growth on Subcutaneous Xenograft and Metastatic Models of Human Melanoma For the subcutaneous tumor model, harvest, wash and resuspend 624mel cultured cells in a 50/50 solution of Matrigel and RPMI 1640 media (10% FBS heat inactivated), then inject $2 \times 10^6$ 624mel cells subcutaneously into the left flank of nude mice. When tumors reach 200 mm$^3$, treat mice with 20D7 or 20D7S, 40 mg/kg twice per week. Measure tumors with calipers twice a week and calculate % T/C. In the 624mel subcutaneous xenograft model, 20D7 inhibited tumor growth T/C=21% and for 20D7S T/C=25%. Both 20D7 and 20D7S inhibited tumor growth in the xenograft model.

For the metastatic model, harvest, wash and resuspend 888mel cultured cells in RPMI 1640 media (10% FBS heat inactivated), inject 888mel cells intravenously. On the second day after the tumor injection, administer to mice anti-TYRP1 antibodies or control human IgG. Sacrifice mice on day 20, remove lungs, count lung surface nodules and calculate percent inhibition. In the metastatic model of 888mel in nude mice, both 20D7 and 20D7S significantly inhibited lung surface metastasis: 20D7 inhibition=77%, p=0.0005; 20D7S inhibition=80%, p=0.0005. Both 20D7 and 20D7S reduced metastasis of melanoma in the metastatic model.

20D7 and Dacarbazine (DTIC) Combination Treatment Demonstrated Stronger Anti-Tumor Activity Compared to Mono-Therapy on Human Xenograft For the subcutaneous model, harvest, wash and resuspend cultured 624mel cells, in a 50/50 solution of Matrigel and RPMI 1640 media (10% FBS heat inactivated). Inject $2 \times 10^6$ 624mel cells into the left flank of nude mice. When tumors reach 200 mm$^3$, treat mice with anti-TYRP1 antibodies, DTIC, or a combination of anti-TYRP1 antibodies and DTIC. Administer 40 mg/kg antibodies once per week. Administer DTIC 5 mg/kg once per week. Measure tumors with calipers twice a week and calculate % T/C. For metastatic model, harvest, wash and resuspend cultured SKmel23, 888mel and B16 melanoma cells, in RPMI 1640 media (10% FBS heat inactivated). Inject SKmel23, 888mel and B16 melanoma cells intravenously. On the second day after the tumor injection, administer to mice anti-TYRP1 antibodies or control human IgG. Sacrifice mice on day 20, remove lungs, count lung surface nodules and calculate percent inhibition.

As demonstrated in the subcutaneous model, 20D7 and DTIC combination treatment inhibited tumor growth significantly better than 20D7 (p<0.001) or DTIC (p<0.001) alone.

TABLE 9

Summary of anti-tumor Activities of 20D7 In Vivo

| Model | Tumor | Measurement | 20D7 | 20D7 + DTIC |
|---|---|---|---|---|
| Metastatic | SKmel23 | % inhibition | 80% | 99%* |
| Metastatic | 888 mel | % inhibition | 77% | 96%* |
| Metastatic | B16 | % inhibition | 95% | ND |
| Subcutaneous | 624mel | % T/C | 50% | 19% |
| | | | P = 0.004 | P < 0.0001 |

Table 9 summarizes in vivo anti-tumor activities of 20D7S compared to monotherapy 20D7 or DTIC in 4 models. The anti-tumor activities of 20D7 in vivo are shown by percent inhibition in metastatic models (the * denotes statistical significance; ND denotes not determined. The anti-tumor activities of 20D7 in vivo are shown by percent T/C in subcutaneous models. Treatment with 20D7 and Dacarbazine (DTIC) in combination demonstrated stronger anti-tumor activity as compared to mono-therapy.

We claim:

1. A monoclonal antibody that specifically binds human TYRP1 (SEQ ID NO. 28), comprising the VH comprising the amino acid sequence:

QVQLVQSGSELKKPGASVKISCKASGYTFTSYAM-NWVRQAPGQGLESMGWINTNTGNPTYAQGFT-GRFVFSMDTSVSTAYLQISSLKAEDTAIYYCAPR-YSSSWYLDYWGQGTLVTVSS (SEQ ID NO: 14), the CDRL1 having the sequence RASQSVSSYLA (SEQ ID NO:4), the CDRL2 having the sequence DASNRAT (SEQ ID NO:5), and the CDRL3 having the sequence QQRSNWLMYT (SEQ ID NO:6).

2. The antibody of claim 1, comprising the VL comprising the amino acid sequence:

EIVLTQSPATLSLSPGERATLSCRASQSVSSYLAWY-QQKPGQAPRLLIYDASNRATGIPARFSGSGSGTD-FTLTISSLEPEDFAVYYCQQRSNWLMYTFGQGT-KLEIK (SEQ ID NO: 16), and the VH comprising the amino acid sequence:

QVQLVQSGSELKKPGASVKISCKASGYTFTSYAM-NWVRQAPGQGLESMGWINTNTGNPTYAQGFT-GRFVFSMDTSVSTAYLQISSLKAEDTAIYYCAPR-YSSSWYLDYWGQGTLVTVSS (SEQ ID NO: 14).

3. The antibody of claim 2, comprising a heavy chain of SEQ ID NO: 30 and a light chain of SEQ ID NO: 32.

4. The antibody of claim 3, comprising two heavy chains of SEQ ID NO: 30 and two light chains of SEQ ID NO: 32.

5. A pharmaceutical composition comprising the antibody of claim 3 together with a pharmaceutically acceptable carrier, diluent or excipient.

6. A method of treating cancer in a patient comprising administering to the patient an effective amount of the antibody of claim 3.

7. The method of claim 6, further comprising administering an effective amount of another anti-neoplastic agent or providing another anti-neoplastic treatment to the patient.

8. The method of claim 7, wherein the anti-neoplastic treatment comprises administering an effective amount of dacarbazine.

* * * * *

UNITED STATES PATENT AND TRADEMARK OFFICE
CERTIFICATE OF CORRECTION

| | | |
|---|---|---|
| PATENT NO. | : 7,951,370 B2 | Page 1 of 1 |
| APPLICATION NO. | : 12/401800 | |
| DATED | : May 31, 2011 | |
| INVENTOR(S) | : Paul J. Balderes et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,951,370 B2 | |
| APPLICATION NO. | : 12/401800 | |
| DATED | : May 31, 2011 | |
| INVENTOR(S) | : Paul J. Balderes et al. | |

It is certified that error appears in the above-identified patent and that said Letters Patent is hereby corrected as shown below:

Column 59, Line 8: In Claim 6, delete "claim 3." and insert -- claim 3, wherein the cancer is malignant melanoma. --, therefor.

Signed and Sealed this
Third Day of January, 2012

David J. Kappos
*Director of the United States Patent and Trademark Office*

SEQUENCE LISTING

<160> NUMBER OF SEQ ID NOS: 33

<210> SEQ ID NO 1
<211> LENGTH: 10
<212> TYPE: PRT
<213> ORGANISM: Homo sapiens

<400> SEQUENCE: 1

Gly Tyr Thr Phe Thr Ser Tyr Ala Met Asn
1               5                   10

<210> SEQ ID NO 2
<211> LENGTH: 17
<212> TYPE: PRT
<213> ORGANISM: Homo sapiens

<400> SEQUENCE: 2

Trp Ile Asn Thr Asn Thr Gly Asn Pro Thr Tyr Ala Gln Gly Phe Thr
1               5                   10                  15

Gly

<210> SEQ ID NO 3
<211> LENGTH: 10
<212> TYPE: PRT
<213> ORGANISM: Homo sapiens

<400> SEQUENCE: 3

Arg Tyr Ser Ser Ser Trp Tyr Leu Asp Tyr
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Asn Arg Ala Thr
1               5

<210> SEQ ID NO 6
<211> LENGTH: 10
<212> TYPE: PRT
<213> ORGANISM: Homo sapiens

<400> SEQUENCE: 6

Gln Gln Arg Ser Asn Trp Leu Met Tyr Thr
1               5                   10

<210> SEQ ID NO 7
<211> LENGTH: 10
<212> TYPE: PRT
<213> ORGANISM: Mus musculus

<400> SEQUENCE: 7

Gly Phe Asn Ile Lys Asp Tyr Phe Leu His
1               5                   10

<210> SEQ ID NO 8
<211> LENGTH: 17
<212> TYPE: PRT
<213> ORGANISM: Mus musculus

<400> SEQUENCE: 8

Trp Ile Asn Pro Asp Asn Gly Asn Thr Val Tyr Asp Pro Lys Phe Gln
1               5                   10                  15

Gly

```
<210> SEQ ID NO 9
<211> LENGTH: 11
<212> TYPE: PRT
<213> ORGANISM: Mus musculus

<400> SEQUENCE: 9

Asp Tyr Thr Tyr Glu Lys Ala Ala Leu Asp Tyr
1               5                   10

<210> SEQ ID NO 10
<211> LENGTH: 11
<212> TYPE: PRT
<213> ORGANISM: Mus musculus

<400> SEQUENCE: 10

Arg Ala Ser Gly Asn Ile Tyr Asn Tyr Leu Ala
1               5                   10

<210> SEQ ID NO 11
<211> LENGTH: 7
<212> TYPE: PRT
<213> ORGANISM: Mus musculus

<400> SEQUENCE: 11

Asp Ala Lys Thr Leu Ala Asp
1               5

<210> SEQ ID NO 12
<211> LENGTH: 9
<212> TYPE: PRT
<213> ORGANISM: Mus musculus

<400> SEQUENCE: 12

Gln His Phe Trp Ser Leu Pro Phe Thr
1               5

<210> SEQ ID NO 13
<211> LENGTH: 119
<212> TYPE: PRT
<213> ORGANISM: Homo sapiens

<400> SEQUENCE: 13

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Ser Tyr
                20                  25                  30

Ala Met Asn Trp Val Arg Gln Ala Pro Gly Gln Gly Leu Glu Cys Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Met Asp Thr Ser Val Ser Thr Ala Tyr
65                  70                  75                  80

Leu Gln Ile Ser Ser Leu Lys Ala Glu Asp Thr Ala Ile Tyr Tyr Cys
                85                  90                  95

Ala Pro Arg Tyr Ser Ser Ser Trp Tyr Leu Asp Tyr Trp Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Homo sapiens
```

```
<400> SEQUENCE: 14

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Ser Tyr
            20                  25                  30

Ala Met Asn Trp Val Arg Gln Ala Pro Gly Gln Gly Leu Glu Ser Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Met Asp Thr Ser Val Ser Thr Ala Tyr
65                  70                  75                  80

Leu Gln Ile Ser Ser Leu Lys Ala Glu Asp Thr Ala Ile Tyr Tyr Cys
                85                  90                  95

Ala Pro Arg Tyr Ser Ser Ser Trp Tyr Leu Asp Tyr Trp Gly Gln Gly
            100                 105                 110

Thr Leu Val Thr Val Ser Ser
        115

<210> SEQ ID NO 15
<211> LENGTH: 122
<212> TYPE: PRT
<213> ORGANISM: Mus musculus

<400> SEQUENCE: 15

Glu Val Gln Leu Gln Gln Ser Gly Ala Glu Leu Val Arg Pro Gly Ala
1               5                   10                  15

Leu Val Lys Leu Ser Cys Lys Thr Ser Gly Phe Asn Ile Lys Asp Tyr
            20                  25                  30

Phe Leu His Trp Val Arg Gln Arg Pro Asp Gln Gly Leu Glu Trp Ile
        35                  40                  45

Gly Trp Ile Asn Pro Asp Asn Gly Asn Thr Val Tyr Asp Pro Lys Phe
    50                  55                  60

Gln Gly Thr Ala Ser Leu Thr Ala Asp Thr Ser Ser Asn Thr Val Tyr
65                  70                  75                  80

Leu Gln Leu Ser Gly Leu Thr Ser Glu Asp Thr Ala Val Tyr Phe Cys
                85                  90                  95

Thr Arg Arg Asp Tyr Thr Tyr Glu Lys Ala Ala Leu Asp Tyr Trp Gly
            100                 105                 110

Gln Gly Ala Ser Val Ile Val Phe Ser Ala
        115                 120

<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Arg Ser Asn Trp Leu Met
                85                  90                  95
Tyr Thr Phe Gly Gln Gly Thr Lys Leu Glu Ile Lys
            100                 105
```

<210> SEQ ID NO 17
<211> LENGTH: 107
<212> TYPE: PRT
<213> ORGANISM: Mus musculus

<400> SEQUENCE: 17

```
Ala Ile Gln Met Ser Gln Ser Pro Ala Ser Leu Ser Ala Ser Val Gly
1               5                   10                  15
Glu Thr Val Thr Ile Thr Cys Arg Ala Ser Gly Asn Ile Tyr Asn Tyr
                20                  25                  30
Leu Ala Trp Tyr Gln Gln Lys Gln Gly Lys Ser Pro His Leu Leu Val
            35                  40                  45
Tyr Asp Ala Lys Thr Leu Ala Asp Gly Val Pro Ser Arg Phe Ser Gly
        50                  55                  60
Ser Gly Ser Gly Thr Gln Tyr Ser Leu Lys Ile Ser Ser Leu Gln Thr
65                  70                  75                  80
Glu Asp Ser Gly Asn Tyr Tyr Cys Gln His Phe Trp Ser Leu Pro Phe
                85                  90                  95
Thr Phe Gly Ser Gly Thr Lys Leu Glu Ile Lys
            100                 105
```

<210> SEQ ID NO 18
<211> LENGTH: 468
<212> TYPE: PRT
<213> ORGANISM: Homo sapiens

<400> SEQUENCE: 18

```
Met Gly Trp Ser Cys Ile Ile Leu Phe Leu Val Ala Thr Ala Thr Gly
1               5                   10                  15
Val His Ser Gln Val Gln Leu Val Gln Ser Gly Ser Glu Leu Lys Lys
                20                  25                  30
Pro Gly Ala Ser Val Lys Ile Ser Cys Lys Ala Ser Gly Tyr Thr Phe
            35                  40                  45
Thr Ser Tyr Ala Met Asn Trp Val Arg Gln Ala Pro Gly Gln Gly Leu
        50                  55                  60
Glu Cys Met Gly Trp Ile Asn Thr Asn Thr Gly Asn Pro Thr Tyr Ala
65                  70                  75                  80
Gln Gly Phe Thr Gly Arg Phe Val Phe Ser Met Asp Thr Ser Val Ser
                85                  90                  95
Thr Ala Tyr Leu Gln Ile Ser Ser Leu Lys Ala Glu Asp Thr Ala Ile
                100                 105                 110
Tyr Tyr Cys Ala Pro Arg Tyr Ser Ser Ser Trp Tyr Leu Asp Tyr Trp
            115                 120                 125
Gly Gln Gly Thr Leu Val Thr Val Ser Ser Ala Ser Thr Lys Gly Pro
        130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
```

```
Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 19
<211> LENGTH: 468
<212> TYPE: PRT
<213> ORGANISM: Artificial Sequence
<220> FEATURE:
<223> OTHER INFORMATION: Synthetic Construct

<400> SEQUENCE: 19

Met Gly Trp Ser Cys Ile Ile Leu Phe Leu Val Ala Thr Ala Thr Gly
1               5                   10                  15

Val His Ser Gln Val Gln Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Ser Tyr Ala Met Asn Trp Val Arg Gln Ala Pro Gly Gln Gly Leu
    50                  55                  60

Glu Ser Met Gly Trp Ile Asn Thr Asn Thr Gly Asn Pro Thr Tyr Ala
65                  70                  75                  80
```

Gln Gly Phe Thr Gly Arg Phe Val Phe Ser Met Asp Thr Ser Val Ser
                85                  90                  95

Thr Ala Tyr Leu Gln Ile Ser Ser Leu Lys Ala Glu Asp Thr Ala Ile
            100                 105                 110

Tyr Tyr Cys Ala Pro Arg Tyr Ser Ser Trp Tyr Leu Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 20
<211> LENGTH: 471
<212> TYPE: PRT
<213> ORGANISM: Artificial Sequence -continued

```
<220> FEATURE:
<223> OTHER INFORMATION: Synthetic Construct

<400> SEQUENCE: 20

Met Gly Trp Ser Cys Ile Ile Leu Phe Leu Val Ala Thr Ala Thr Gly
1               5                   10                  15

Val His Ser Glu Val Gln Leu Gln Gln Ser Gly Ala Glu Leu Val Arg
            20                  25                  30

Pro Gly Ala Leu Val Lys Leu Ser Cys Lys Thr Ser Gly Phe Asn Ile
        35                  40                  45

Lys Asp Tyr Phe Leu His Trp Val Arg Gln Arg Pro Asp Gln Gly Leu
    50                  55                  60

Glu Trp Ile Gly Trp Ile Asn Pro Asp Asn Gly Asn Thr Val Tyr Asp
65                  70                  75                  80

Pro Lys Phe Gln Gly Thr Ala Ser Leu Thr Ala Asp Thr Ser Ser Asn
                85                  90                  95

Thr Val Tyr Leu Gln Leu Ser Gly Leu Thr Ser Glu Asp Thr Ala Val
            100                 105                 110

Tyr Phe Cys Thr Arg Arg Asp Tyr Thr Tyr Glu Lys Ala Ala Leu Asp
        115                 120                 125

Tyr Trp Gly Gln Gly Ala Ser Val Ile Val Phe Ser Ala Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400
```

```
Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys
465             470

<210> SEQ ID NO 21
<211> LENGTH: 1407
<212> TYPE: DNA
<213> ORGANISM: Homo sapiens

<400> SEQUENCE: 21
atgggatggt catgtatcat ccttttcta gtagcaactg caactggagt acattcacag     60
gtgcagctgg tccaatctgg gtctgagttg aagaagcctg gggcctcagt gaagatttcc   120
tgcaaggctt ctggatacac cttcactagc tatgctatga attgggtgcg acaggccct   180 ggacaagggc ttgagtgtat gggatggatc aacaccaaca ctgggaaccc aacgtatgcc   240
cagggcttca caggacggtt tgtcttctcc atggacacct tgtcagcac ggcatatctg   300 cagatcagca gcctaaaggc tgaggacact gccatatatt actgtgcgcc cgatatagc   360 agcagctggt accttgatta ctggggccag ggaaccctgg tcaccgtgtc ctcagctagc   420
accaagggcc atcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660 tgcaacgtga atcacaagcc cagcaacacc aaggtggaca agagagttga gcccaaatct   720
tgtgacaaaa ctcacacatg cccaccgtgc ccagcacctg aactcctggg gggaccgtca   780
gtcttcctct ccccccaaa cccaaggac accctcatga tctcccggac ccctgaggtc   840
acatgcgtgg tggtggacgt gagccacgaa gaccctgagg tcaagttcaa ctggtatgtg   900
gacggcgtgg aggtgcataa tgccaagaca aagccgcggg aggagcagta caacagcacg   960
taccgtgtgg tcagcgtcct caccgtcctg caccaagact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga ggagatgacc  1140
aagaaccaag tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctattccaag ctcaccgtgg acaagagcag gtggcagcag  1320
gggaacgtct tctcatgctc cgtgatgcat gaggctctgc acaaccacta cacgcagaag  1380
agcctctccc tgtctccggg caaatga                                      1407

<210> SEQ ID NO 22
<211> LENGTH: 1407
<212> TYPE: DNA
<213> ORGANISM: Artificial Sequence
<220> FEATURE:
<223> OTHER INFORMATION: Synthetic Construct
```

<400> SEQUENCE: 22

```
atgggatggt catgtatcat ccttttcta gtagcaactg caactggagt acattcacag    60
gtgcagctgg tccaatctgg gtctgagttg aagaagcctg ggcctcagt gaagatttcc   120
tgcaaggctt ctggatacac cttcactagc tatgctatga attgggtgcg acaggcccct   180
ggacaagggc ttgagtctat gggatggatc aacaccaaca ctgggaaccc aacgtatgcc   240
cagggcttca caggacggtt tgtcttctcc atggacacct ctgtcagcac ggcatatctg   300
cagatcagca gcctaaaggc tgaggacact gccatatatt actgtgcgcc ccgatatagc   360
agcagctggt accttgatta ctggggccag ggaaccctgg tcaccgtgtc ctcagctagc   420
accaagggcc catcggtctt ccccctggca ccctcctcca gagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcacccca gacctacatc   660
tgcaacgtga atcacaagcc cagcaacacc aaggtggaca agagagttga gcccaaatct   720
tgtgacaaaa ctcacacatg cccaccgtgc ccagcacctg aactcctggg gggaccgtca   780
gtcttcctct tcccccccaaa acccaaggac accctcatga tctcccggac ccctgaggtc   840
acatgcgtgg tggtggacgt gagccacgaa gaccctgagg tcaagttcaa ctggtatgtg   900
gacggcgtgg aggtgcataa tgccaagaca agccgcggg aggagcagta caacagcacg   960
taccgtgtgg tcagcgtcct caccgtcctg caccaagact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga ggagatgacc  1140
aagaaccaag tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctattccaag ctcaccgtgg acaagagcag gtggcagcag  1320
gggaacgtct tctcatgctc cgtgatgcat gaggctctgc acaaccacta cacgcagaag  1380
agcctctccc tgtctccggg caaatga                                      1407
```

<210> SEQ ID NO 23
<211> LENGTH: 1413
<212> TYPE: DNA
<213> ORGANISM: Artificial Sequence
<220> FEATURE:
<223> OTHER INFORMATION: Synthetic Construct

<400> SEQUENCE: 23

```
atgggatggt catgtatcat ccttttcta gtagcaactg caactggagt acattcagag    60
gttcagctgc agcagtctgg ggctgagctt gtgaggccag ggccttggt caagttgtcc   120
tgcaaaactt ctggcttcaa cattaaagac tactttttac actgggtgag acagaggcct   180
gaccagggcc tggagtggat tggatggatt aatcctgata atggtaatac tgtttatgac   240
ccgaagtttc agggcacggc cagtttaaca gcagacacat cctccaacac agtctacttg   300
cagctcagcg gcctgacatc tgaggacact gccgtctatt tctgtactcg agggactat   360
acttatgaaa aggctgctct ggactactgg ggtcagggag cctcagtcat cgtctcctca   420
gctagcacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
```

-continued

```
ggactctact ccctcagcag cgtggtgacc gtgccctcca gcagcttggg cacccagacc    660
tacatctgca acgtgaatca caagcccagc aacaccaagg tggacaagag agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tatgtggacg gcgtggaggt gcataatgcc aagacaaagc cgcgggagga gcagtacaac    960
agcacgtacc gtgtggtcag cgtcctcacc gtcctgcacc aagactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggaggag   1140
atgaccaaga accaagtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctat tccaagctca ccgtggacaa gagcaggtgg   1320
cagcagggga acgtcttctc atgctccgtg atgcatgagg ctctgcacaa ccactacacg   1380
cagaagagcc tctccctgtc tccgggcaaa tga                                1413
```

<210> SEQ ID NO 24
<211> LENGTH: 234
<212> TYPE: PRT
<213> ORGANISM: Homo sapiens

<400> SEQUENCE: 24

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Leu Met Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 25
<211> LENGTH: 233
<212> TYPE: PRT
<213> ORGANISM: Artificial Sequence
<220> FEATURE:
<223> OTHER INFORMATION: Synthetic Construct

<400> SEQUENCE: 25

```
Met Gly Trp Ser Cys Ile Ile Leu Phe Leu Val Ala Thr Ala Thr Gly
1               5                   10                  15

Val His Ser Ala Ile Gln Met Ser Gln Ser Pro Ala Ser Leu Ser Ala
            20                  25                  30

Ser Val Gly Glu Thr Val Thr Ile Thr Cys Arg Ala Ser Gly Asn Ile
        35                  40                  45

Tyr Asn Tyr Leu Ala Trp Tyr Gln Gln Lys Gln Gly Lys Ser Pro His
    50                  55                  60

Leu Leu Val Tyr Asp Ala Lys Thr Leu Ala Asp Gly Val Pro Ser Arg
65                  70                  75                  80

Phe Ser Gly Ser Gly Ser Gly Thr Gln Tyr Ser Leu Lys Ile Ser Ser
                85                  90                  95

Leu Gln Thr Glu Asp Ser Gly Asn Tyr Tyr Cys Gln His Phe Trp Ser
            100                 105                 110

Leu Pro Phe Thr Phe Gly Ser Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 26
<211> LENGTH: 705
<212> TYPE: DNA
<213> ORGANISM: Homo sapiens

<400> SEQUENCE: 26

| | | | | |
|---|---|---|---|---|
| atgggatggt | catgtatcat | ccttttttcta | gtagcaactg | caactggagt acattcagaa | 60 |
| attgtgttga | cacagtctcc | agccaccctg | tctttgtctc | caggggaaag agccaccctc | 120 |
| tcctgcaggg | ccagtcagag | tgttagcagc | tacttagcct | ggtaccaaca gaaacctggc | 180 |
| caggctccca | ggctcctcat | ctatgatgca | tccaacaggg | ccactggcat cccagccagg | 240 |
| ttcagtggca | gtgggtctgg | gacagactte | actctcacca | tcagcagcct agagcctgaa | 300 |
| gattttgcag | tttattactg | tcagcagcgt | agcaactggc | tcatgtacac ttttggccag | 360 |
| gggaccaagc | tggagatcaa | acgaactgtg | gctgcaccat | ctgtcttcat cttcccgcca | 420 |
| tctgatgagc | agttgaaatc | tggaactgcc | tctgttgtgt | gcctgctgaa taacttctat | 480 |
| cccagagagg | ccaaagtaca | gtggaaggtg | gataacgccc | tccaatcggg taactcccag | 540 |

```
gagagtgtca cagagcagga cagcaaggac agcacctaca gcctcagcag caccctgacg    600
ctgagcaaag cagactacga aaacacaaa gtctacgcct gcgaagtcac ccatcagggc     660
ctgagctcgc ccgtcacaaa gagcttcaac aggggagagt gttag                    705
```

<210> SEQ ID NO 27
<211> LENGTH: 702
<212> TYPE: DNA
<213> ORGANISM: Artificial Sequence
<220> FEATURE:
<223> OTHER INFORMATION: Synthetic Construct

<400> SEQUENCE: 27

```
atgggatggt catgtatcat ccttttttcta gtagcaactg caactggagt acattcagcc    60
atccagatgt ctcagtctcc agcctcccta tctgcatctg tgggagaaac tgtcaccatc    120
acatgtcgag caagtggaaa tatttacaat tatttagcat ggtatcagca gaaacaggga    180
aaatctcctc acctcctggt ctatgatgca aaaaccttag cagatggtgt gccatcaagg    240
ttcagtggca gtggctcagg gacacaatat tctctcaaga ttagcagcct gcagactgaa    300
gattctggga attattactg tcaacatttt tggagtcttc cattcacgtt cggctcgggg    360
acaaagttgg aaataaaacg aactgtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                        702
```

<210> SEQ ID NO 28
<211> LENGTH: 537
<212> TYPE: PRT
<213> ORGANISM: Homo sapiens

<400> SEQUENCE: 28

```
Met Ser Ala Pro Lys Leu Leu Ser Leu Gly Cys Ile Phe Phe Pro Leu
1               5                   10                  15

Leu Leu Phe Gln Gln Ala Arg Ala Gln Phe Pro Arg Gln Cys Ala Thr
            20                  25                  30

Val Glu Ala Leu Arg Ser Gly Met Cys Cys Pro Asp Leu Ser Pro Val
        35                  40                  45

Ser Gly Pro Gly Thr Asp Arg Cys Gly Ser Ser Gly Arg Gly Arg
    50                  55                  60

Cys Glu Ala Val Thr Ala Asp Ser Arg Pro His Ser Pro Gln Tyr Pro
65                  70                  75                  80

His Asp Gly Arg Asp Asp Arg Glu Val Trp Pro Leu Arg Phe Asn
                85                  90                  95

Arg Thr Cys His Cys Asn Gly Asn Phe Ser Gly His Asn Cys Gly Thr
            100                 105                 110

Cys Arg Pro Gly Trp Arg Gly Ala Ala Cys Asp Gln Arg Val Leu Ile
        115                 120                 125

Val Arg Arg Asn Leu Leu Asp Leu Ser Lys Glu Glu Lys Asn His Phe
    130                 135                 140

Val Arg Ala Leu Asp Met Ala Lys Arg Thr Thr His Pro Leu Phe Val
145                 150                 155                 160
```

Ile Ala Thr Arg Arg Ser Glu Glu Ile Leu Gly Pro Asp Gly Asn Thr
            165                 170                 175

Pro Gln Phe Glu Asn Ile Ser Ile Tyr Asn Tyr Phe Val Trp Thr His
        180                 185                 190

Tyr Tyr Ser Val Lys Lys Thr Phe Leu Gly Val Gly Gln Glu Ser Phe
        195                 200                 205

Gly Glu Val Asp Phe Ser His Glu Gly Pro Ala Phe Leu Thr Trp His
    210                 215                 220

Arg Tyr His Leu Leu Arg Leu Glu Lys Asp Met Gln Glu Met Leu Gln
225                 230                 235                 240

Glu Pro Ser Phe Ser Leu Pro Tyr Trp Asn Phe Ala Thr Gly Lys Asn
                245                 250                 255

Val Cys Asp Ile Cys Thr Asp Leu Met Gly Ser Arg Ser Asn Phe
            260                 265                 270

Asp Ser Thr Leu Ile Ser Pro Asn Ser Val Phe Ser Gln Trp Arg Val
        275                 280                 285

Val Cys Asp Ser Leu Glu Asp Tyr Asp Thr Leu Gly Thr Leu Cys Asn
    290                 295                 300

Ser Thr Glu Asp Gly Pro Ile Arg Arg Asn Pro Ala Gly Asn Val Ala
305                 310                 315                 320

Arg Pro Met Val Gln Arg Leu Pro Glu Pro Gln Asp Val Ala Gln Cys
                325                 330                 335

Leu Glu Val Gly Leu Phe Asp Thr Pro Pro Phe Tyr Ser Asn Ser Thr
            340                 345                 350

Asn Ser Phe Arg Asn Thr Val Glu Gly Tyr Ser Asp Pro Thr Gly Lys
        355                 360                 365

Tyr Asp Pro Ala Val Arg Ser Leu His Asn Leu Ala His Leu Phe Leu
    370                 375                 380

Asn Gly Thr Gly Gly Gln Thr His Leu Ser Pro Asn Asp Pro Ile Phe
385                 390                 395                 400

Val Leu Leu His Thr Phe Thr Asp Ala Val Phe Asp Glu Trp Leu Arg
                405                 410                 415

Arg Tyr Asn Ala Asp Ile Ser Thr Phe Pro Leu Glu Asn Ala Pro Ile
            420                 425                 430

Gly His Asn Arg Gln Tyr Asn Met Val Pro Phe Trp Pro Pro Val Thr
        435                 440                 445

Asn Thr Glu Met Phe Val Thr Ala Pro Asp Asn Leu Gly Tyr Thr Tyr
    450                 455                 460

Glu Ile Gln Trp Pro Ser Arg Glu Phe Ser Val Pro Glu Ile Ile Ala
465                 470                 475                 480

Ile Ala Val Val Gly Ala Leu Leu Leu Val Ala Leu Ile Phe Gly Thr
                485                 490                 495

Ala Ser Tyr Leu Ile Arg Ala Arg Arg Ser Met Asp Glu Ala Asn Gln
            500                 505                 510

Pro Leu Leu Thr Asp Gln Tyr Gln Cys Tyr Ala Glu Glu Tyr Glu Lys
        515                 520                 525

Leu Gln Asn Pro Asn Gln Ser Val Val
    530                 535

<210> SEQ ID NO 29
<211> LENGTH: 449
<212> TYPE: PRT
<213> ORGANISM: Homo sapiens

<400> SEQUENCE: 29

```
Gln Val Gln Leu Val Gln Ser Gly Ser Glu Leu Lys Lys Pro Gly Ala
  1               5                  10                  15
Ser Val Lys Ile Ser Cys Lys Ala Ser Gly Tyr Thr Phe Thr Ser Tyr
             20                  25                  30
Ala Met Asn Trp Val Arg Gln Ala Pro Gly Gln Gly Leu Glu Cys Met
         35                  40                  45
Gly Trp Ile Asn Thr Asn Thr Gly Asn Pro Thr Tyr Ala Gln Gly Phe
     50                  55                  60
Thr Gly Arg Phe Val Phe Ser Met Asp Thr Ser Val Ser Thr Ala Tyr
 65                  70                  75                  80
Leu Gln Ile Ser Ser Leu Lys Ala Glu Asp Thr Ala Ile Tyr Tyr Cys
                 85                  90                  95
Ala Pro Arg Tyr Ser Ser Trp Tyr Leu Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 30
<211> LENGTH: 449
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Ser Tyr
            20                  25                  30

Ala Met Asn Trp Val Arg Gln Ala Pro Gly Gln Gly Leu Glu Ser Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Met Asp Thr Ser Val Ser Thr Ala Tyr
65                  70                  75                  80

Leu Gln Ile Ser Ser Leu Lys Ala Glu Asp Thr Ala Ile Tyr Tyr Cys
                85                  90                  95

Ala Pro Arg Tyr Ser Ser Ser Trp Tyr Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

-continued

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 31
<211> LENGTH: 452
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Gln Gln Ser Gly Ala Glu Leu Val Arg Pro Gly Ala
1               5                   10                  15

Leu Val Lys Leu Ser Cys Lys Thr Ser Gly Phe Asn Ile Lys Asp Tyr
            20                  25                  30

Phe Leu His Trp Val Arg Gln Arg Pro Asp Gln Gly Leu Glu Trp Ile
        35                  40                  45

Gly Trp Ile Asn Pro Asp Asn Gly Asn Thr Val Tyr Asp Pro Lys Phe
    50                  55                  60

Gln Gly Thr Ala Ser Leu Thr Ala Asp Thr Ser Ser Asn Thr Val Tyr
65                  70                  75                  80

Leu Gln Leu Ser Gly Leu Thr Ser Glu Asp Thr Ala Val Tyr Phe Cys
                85                  90                  95

Thr Arg Arg Asp Tyr Thr Tyr Glu Lys Ala Ala Leu Asp Tyr Trp Gly
            100                 105                 110

Gln Gly Ala Ser Val Ile Val Phe Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 32
<211> LENGTH: 215
<212> TYPE: PRT
<213> ORGANISM: Homo sapiens

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Met
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

-continued

```
Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 33
<211> LENGTH: 214
<212> TYPE: PRT
<213> ORGANISM: Artificial Sequence
<220> FEATURE:
<223> OTHER INFORMATION: Synthetic Construct

<400> SEQUENCE: 33

Ala Ile Gln Met Ser Gln Ser Pro Ala Ser Leu Ser Ala Ser Val Gly
1               5                   10                  15

Glu Thr Val Thr Ile Thr Cys Arg Ala Ser Gly Asn Ile Tyr Asn Tyr
            20                  25                  30

Leu Ala Trp Tyr Gln Gln Lys Gln Gly Lys Ser Pro His Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Ser Ser Leu Gln Thr
65                  70                  75                  80

Glu Asp Ser Gly Asn Tyr Tyr Cys Gln His Phe Trp Ser Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```